(12) United States Patent
Bartsch (10) Patent No.: US 9,364,701 B2
(45) Date of Patent: Jun. 14, 2016

(54) DEVICE AND METHODS FOR ACCESSORY CHEST MUSCLE DEVELOPMENT

(75) Inventor: Darwyn Bartsch, Chandler, AZ (US)

(73) Assignee: Upper Core Technologies, LLC, Chandler, AZ (US)

(*) Notice: Subject to any disclaimer, the term of this patent is extended or adjusted under 35 U.S.C. 154(b) by 944 days.

(21) Appl. No.: 13/094,683

(22) Filed: Apr. 26, 2011

(65) Prior Publication Data

US 2012/0277073 A1    Nov. 1, 2012

(51) Int. Cl.
| | |
|---|---|
| *A63B 23/02* | (2006.01) |
| *A61F 5/03* | (2006.01) |
| *A63B 21/055* | (2006.01) |
| *A61F 5/02* | (2006.01) |
| *A61F 13/14* | (2006.01) |
| *A63B 23/18* | (2006.01) |
| *A61F 13/00* | (2006.01) |
| *A63B 71/06* | (2006.01) |
| *A63B 21/00* | (2006.01) |

(52) U.S. Cl.
CPC ............... *A63B 21/055* (2013.01); *A61F 5/02* (2013.01); *A61F 5/03* (2013.01); *A61F 13/14* (2013.01); *A61F 13/143* (2013.01); *A63B 21/4007* (2015.10); *A63B 21/4025* (2015.10); *A63B 23/02* (2013.01); *A63B 23/18* (2013.01); *A61F 2013/00493* (2013.01); *A63B 21/00069* (2013.01); *A63B 2071/0694* (2013.01); *A63B 2209/10* (2013.01)

(58) Field of Classification Search
CPC ............. A61F 5/02; A61F 5/03; A61F 13/14; A61F 13/143; A61F 2013/00493; A63B 21/00149; A63B 21/065; A63B 21/1415; A63B 23/02
USPC .................. 602/19, 60, 61, 75; 128/874–876; 482/124, 139; 450/2, 79
See application file for complete search history.

(56) References Cited

U.S. PATENT DOCUMENTS

| | | | |
|---|---|---|---|
| 6,516,804 B1* | 2/2003 | Hoffman | 128/846 |
| 2006/0047236 A1* | 3/2006 | Hansen | 602/4 |
| 2007/0118062 A1* | 5/2007 | Fleck | 602/75 |

* cited by examiner

*Primary Examiner* — Keri J Nelson
(74) *Attorney, Agent, or Firm* — Etherton Law Group, LLC (57) ABSTRACT

A method of developing the accessory muscles of the upper torso utilizes a therapy device having an adjustable compressive wrap that wraps around the chest of a patient. The wrap is made of a substantially elastic material, such as neoprene, and has a releasable fastener to removably attach the wrap to itself around the patient's chest. The device may have one or more markers attached to the wrap to indicate to a therapist where the attachment device should be attached to achieve the desired compression around the chest. The therapist places the device on the patient and tightens the wrap until the therapist determines, by observing the rise and fall of the patient's chest, that the device has activated the patient's accessory muscles. The patient wears the device at this tension for about two hours per day, at least six days per week, for the first two weeks. Then, the tension level is reassessed and the device is worn for about three hours per day, at least six days per week, and the tension is reassessed every four weeks for between 12 and 24 months.

13 Claims, 7 Drawing Sheets

DEVICE AND METHODS FOR ACCESSORY CHEST MUSCLE DEVELOPMENT

FIELD OF INVENTION

This invention relates to muscular therapy devices. This invention relates particularly to a device and method for developing the postural, breathing, and intrinsic muscles of the upper torso.

BACKGROUND

In physical therapy terms, a patient's "chest" is comprised of the skeletal and muscular structures of the upper torso, particularly including the ribcage and spine and the muscles attached to them. In addition to large chest muscles such as the pectoralis, the chest includes small muscles and muscle fibers that aid in breathing, posture, and upper-body motor skills. Collectively, these muscles are referred to as the accessory muscles. The accessory muscles may include the scalene muscles, the sternocleidomastoid muscle, the levatores costarum, the intercostals and subcostals, the transversus thoracis, the serratus posterior superior, and the serratus posterior inferior. The accessory muscles may be compromised by injury, invasive medical procedures, malnutrition, sedentary lifestyle, genetic disposition, or developmental delays that may have been caused as early as the patient's infancy.

A lack of accessory muscle strength or development may lead to health and physical developmental problems ranging from bothersome to very serious. These include bad posture, diminished respiratory capacity and support, speech problems due to lack of breath suspension, increased susceptibility to injury, low agility and athletic performance, undesirable physical appearance, and decreased motor function, particularly in the arms as they would otherwise be supported by the core muscles. Additionally, when the ribcage is not properly supported by the accessory muscles, the application of unequal forces over time may lead to flared ribs and pectus excavatum, also known as sunken chest. A device and therapy method is needed to address the habilitation and rehabilitation of underdeveloped or injured accessory muscles.

In a particular example, recently a link has been shown between underdevelopment of the patient's accessory muscles and a shortage of time the patient spent lying on his stomach during infancy, commonly referred to as "tummy time." During tummy time, an infant's chest works against the resistance of the infant's own weight in order to draw breath into the lungs. This activates the chest muscles associated with breathing and essentially trains the infant to breathe with the chest muscles rather than the stomach muscles alone. This effect is a widely unrecognized benefit of tummy time, which is primarily thought to strengthen the neck and back muscles while the infant learns to hold up and control his head.

It follows that when infants do not get enough tummy time, the chest muscles fail to develop. Historically, 6-12 hours per day of tummy time has been recommended, much of which may be achieved while the infant sleeps. Unfortunately, infants that sleep on their stomachs appear to be more susceptible to sudden infant death syndrome, so parents and caregivers have largely curtailed unsupervised tummy time. Additionally, tummy time may be challenging for infants who have medical problems, such as a compromised respiratory system or gastroesophageal reflux disease. It would be advantageous to provide the developmental benefits of tummy time without the associated dangers to an infant.

Physical therapists currently present intensive, session-based therapy regimens to improve core stability. Most commonly, these regimens include several exercises using a stability ball. Other balance, posture, and lifting exercises using the stability ball may be incorporated to train the core muscles. These regimens are often effective for adults and older children. However, they require continued visits to the therapist several times a week, can be physically intensive, only focus on the larger muscles of the patient's core, and are only developing the muscles at the time of the session. Furthermore, due to the physical exertion and impact of the exercises, these regimens are not appropriate for infants and young children. A program that passively develops the accessory muscles with a minimal interruption to the daily routine of the patient and can be used for patients of all ages is needed.

Some devices for correcting posture are known. Typically, these are some form of brace that provides passive support to the spine. However, these devices do not train accessory muscles, and therefore could not be used to address the problems defined above. Furthermore, these devices are generally for adults and are not often usable for infants or young children. A device that passively trains the chest muscles associated with breathing and posture, specifically the accessory muscles, and can be used for patients of all ages is needed.

Therefore, it is an object of this invention to provide a method and device for developing or rehabilitating the accessory muscles of the upper torso. It is a further object that the method and device be usable by infants, children, and adults. It is a further object that the method and device passively provide a positive developmental effect on a daily basis. It is another object of the invention to provide a method and device that implements a therapeutic regimen to address breathing, speech, posture, and motor skill deficiencies caused by injury to or underdevelopment of the accessory muscles of the upper torso.

SUMMARY OF THE INVENTION

A method of strengthening the accessory muscles of the chest utilizes an adjustable compressive device in a supervised therapy regimen. The device is a wearable article that fits a patient like a vest, wrapping around the chest and shoulders. The device is made of a substantially elastic material, such as natural or synthetic rubber or another polymer, and is most preferably made of neoprene. The device has a releasable fastener, such as VELCRO®, to removably attach the device to itself around the patient's chest. The device may have one or more markers attached to it to indicate to a therapist where the fastener should be attached to achieve the desired compression around the chest.

To strengthen the desired muscles of the patient, the therapist places the device on the patient and secures the fastener so the device is tight around the patient's chest, but is not under tension. The therapist then tightens the device in small increments until the therapist determines, by observing the rise and fall of the patient's chest, that the device has activated the patient's accessory muscles, and the patient is using the middle and upper chest for inspiration and expiration. The patient wears the device at this tension for about two hours per day and at least six days per week for the first two weeks. At the end of this period, the tension level is reassessed and increased if tolerable. The device is then worn for about three hours per day, at least six days per week, and the tension is reassessed every four weeks. The regimen proceeds for, typically, between 12 and 24 months, depending on the desired results.

DETAILED DESCRIPTION OF THE INVENTION

Figure 1:
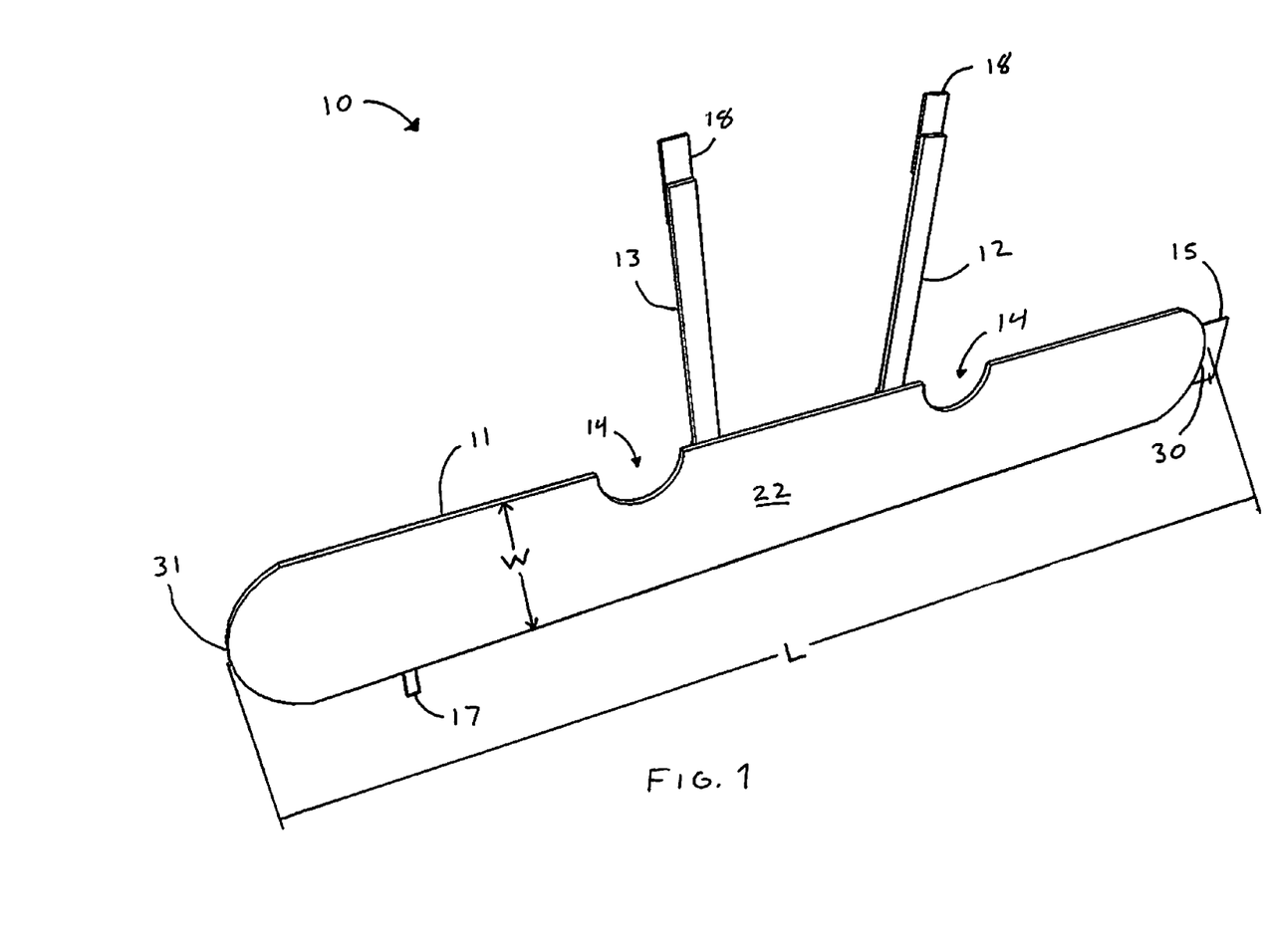
FIG. 1 is a perspective view of the preferred embodiment of the present invention, showing the inner surface of the wrap.
Figure 2:
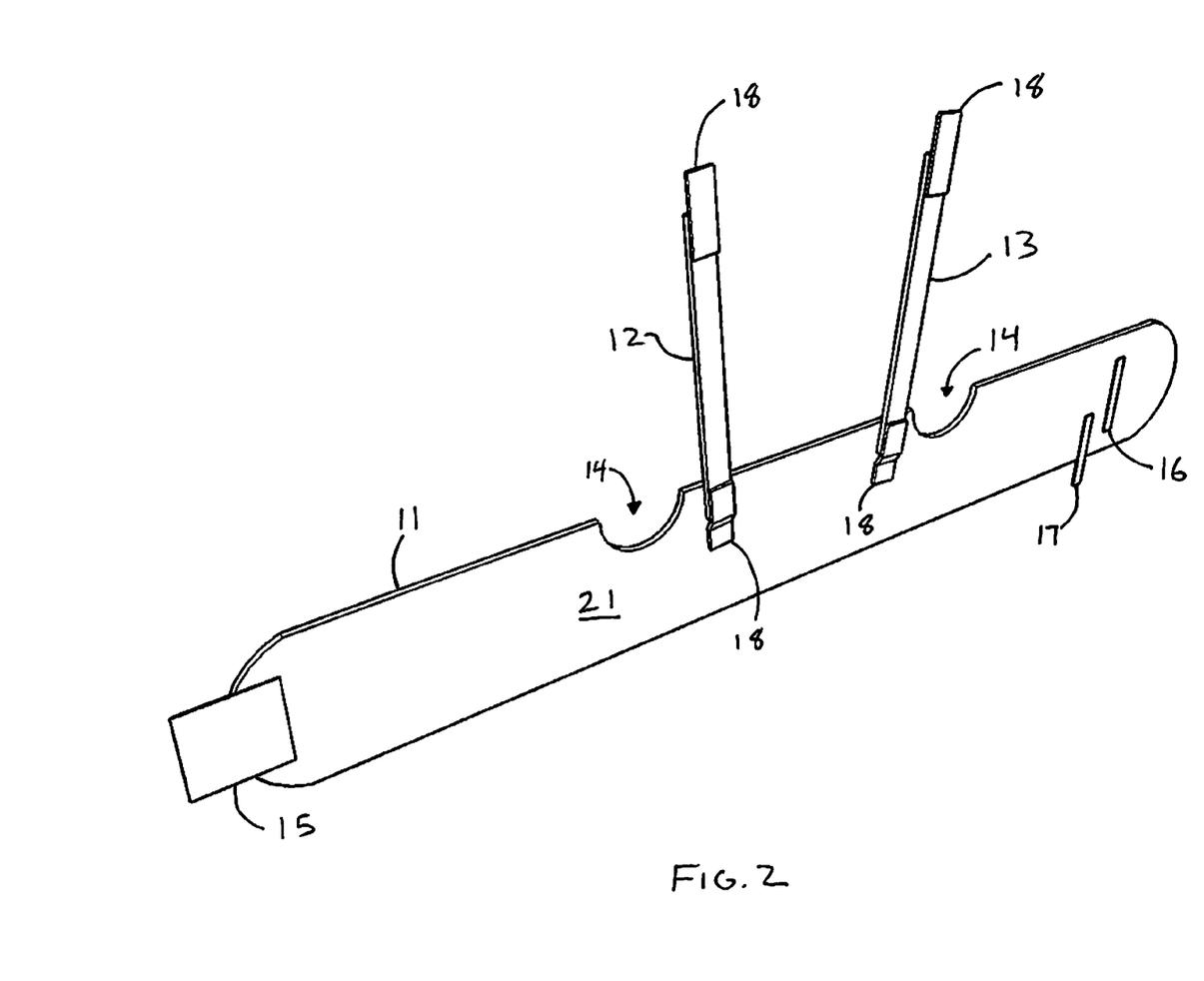
FIG. 2 is a perspective view of the preferred embodiment showing the outer surface of the wrap.
Figure 3:
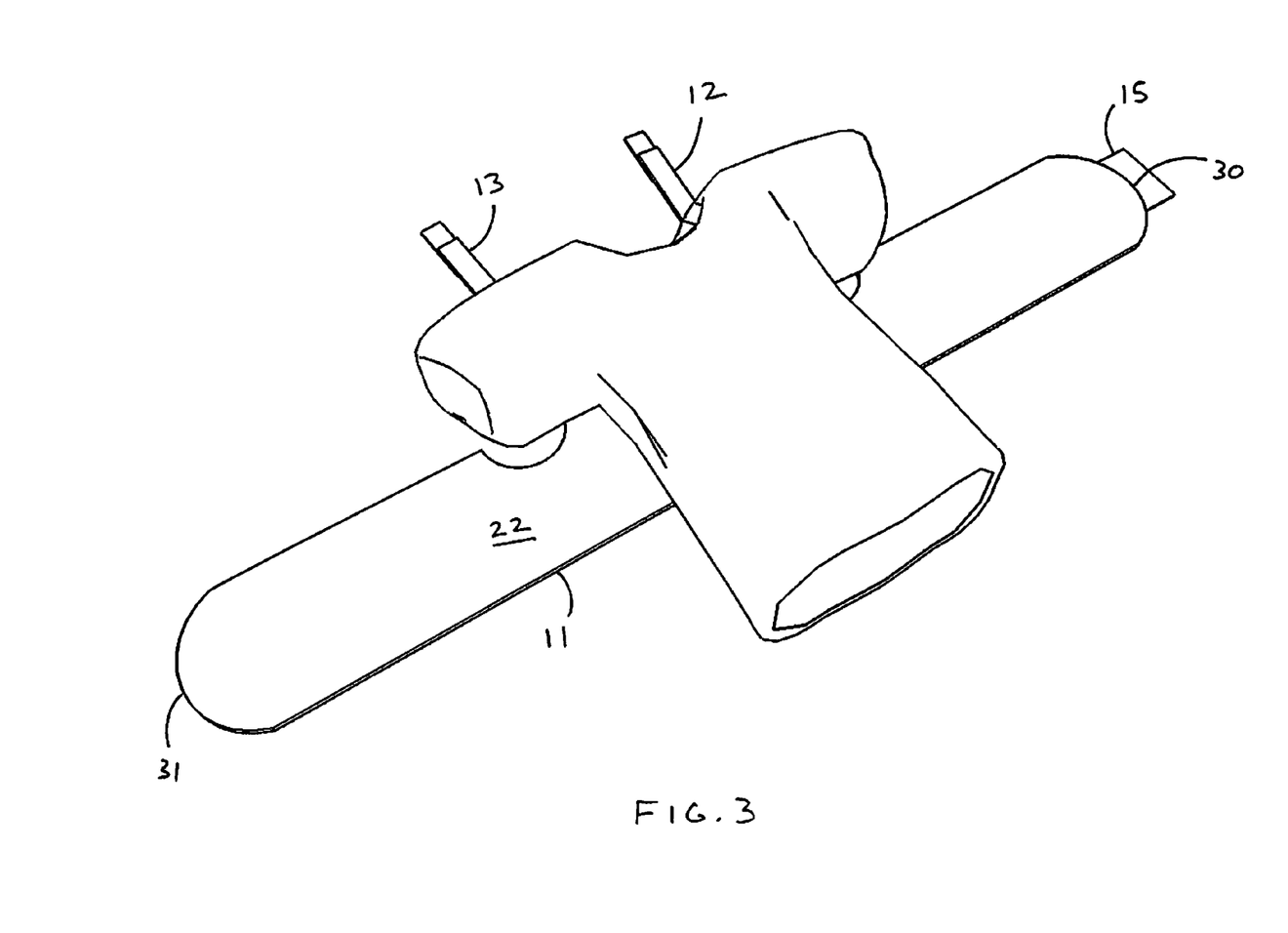
FIG. 3 is a perspective view of the preferred device shown at the first step of the present inventive method, with the patient represented by an illustration of a shirt.
Figure 4:
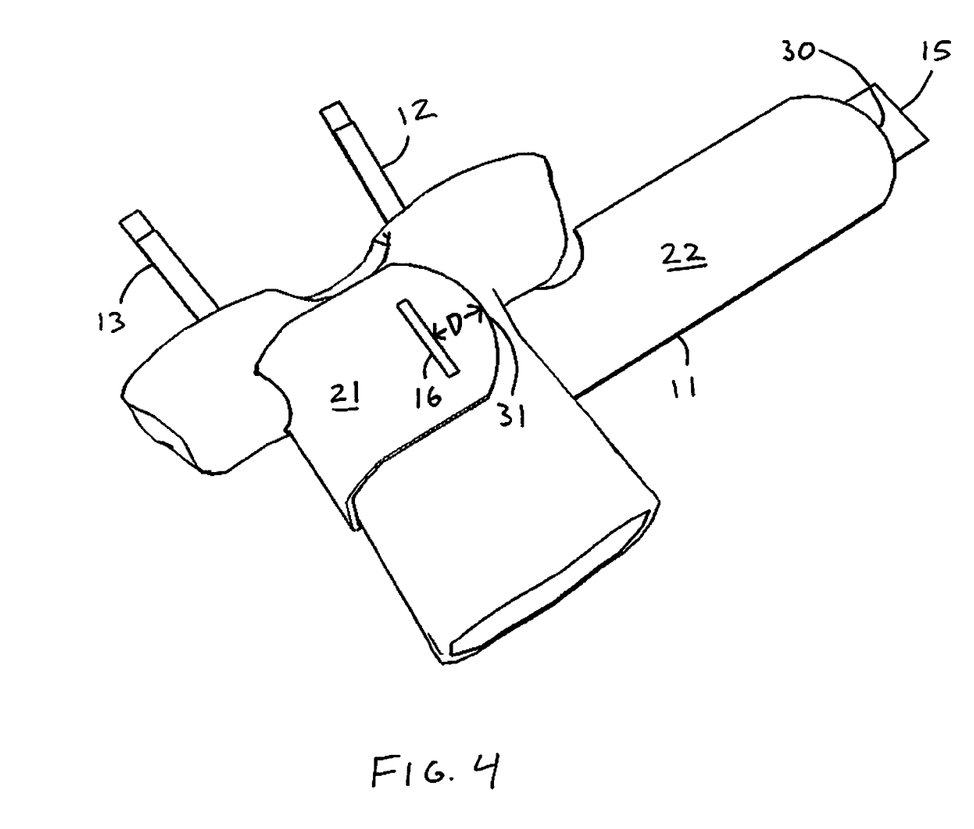
FIG. 4 is a perspective view of the preferred device shown at the second step of the present inventive method, with the patient represented by an illustration of a shirt.
Figure 5:
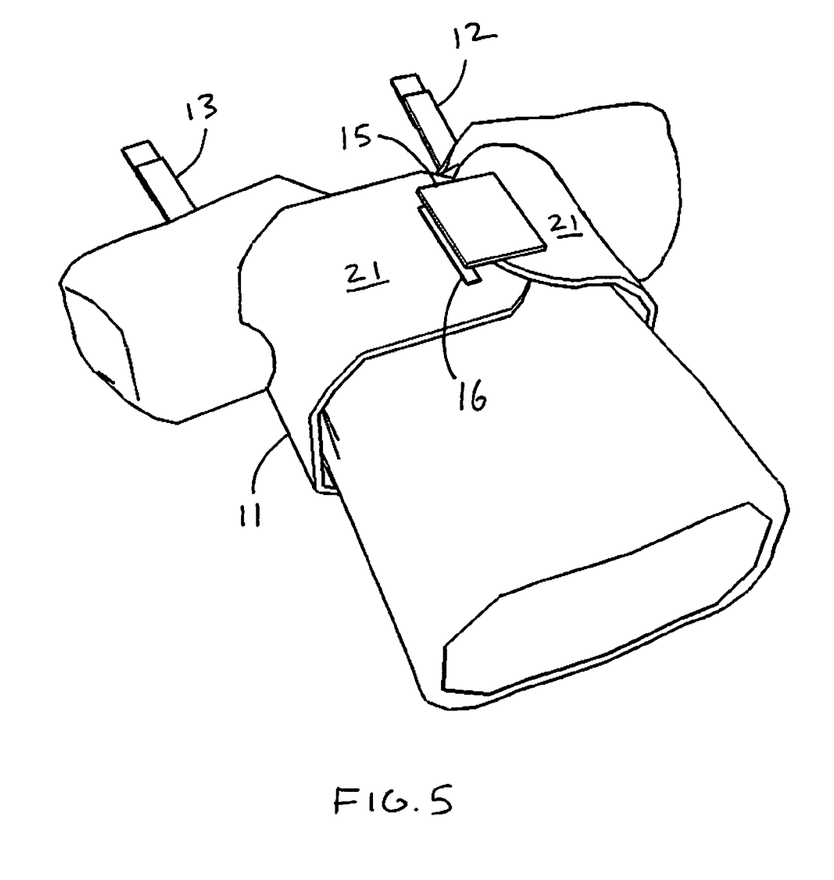
FIG. 5 is a perspective view of the preferred device shown at the third step of the present inventive method, with the patient represented by an illustration of a shirt.
Figure 6:
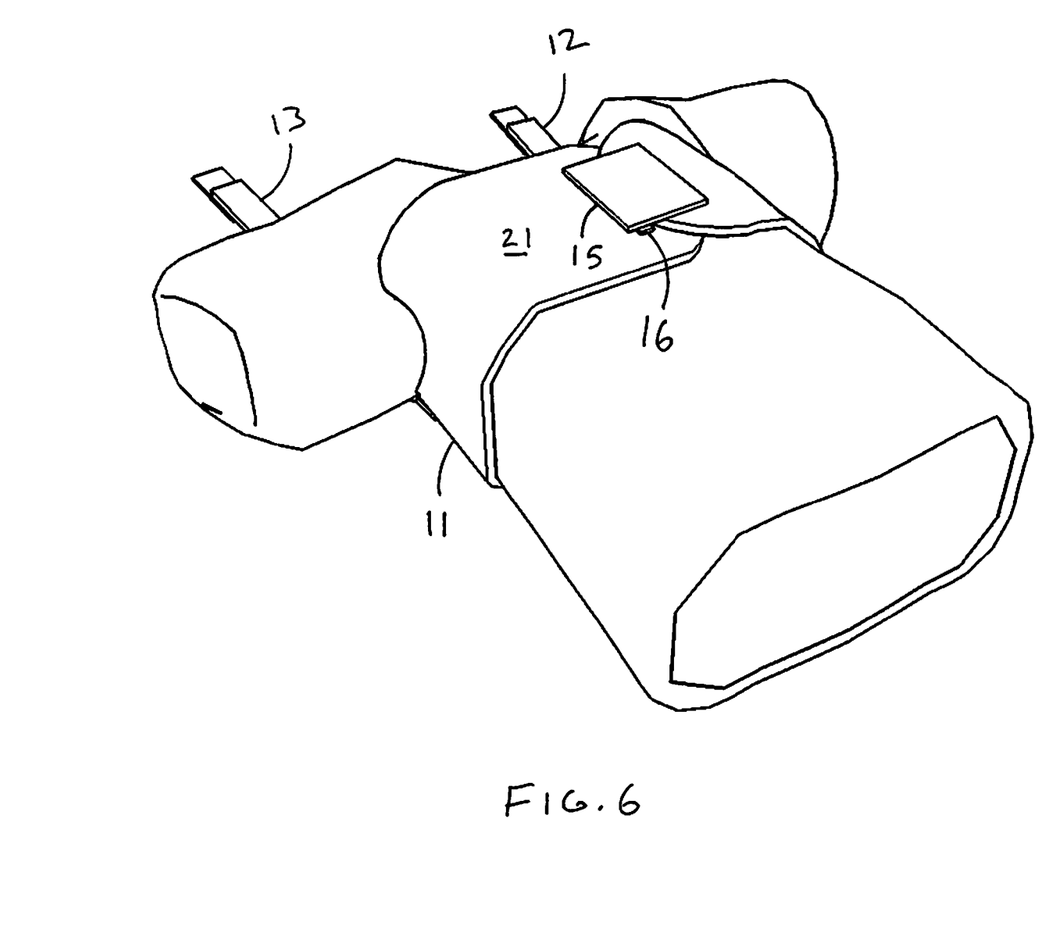
FIG. 6 is a perspective view of the preferred device shown at the fourth step of the present inventive method, with the patient represented by an illustration of a shirt.
Figure 7:
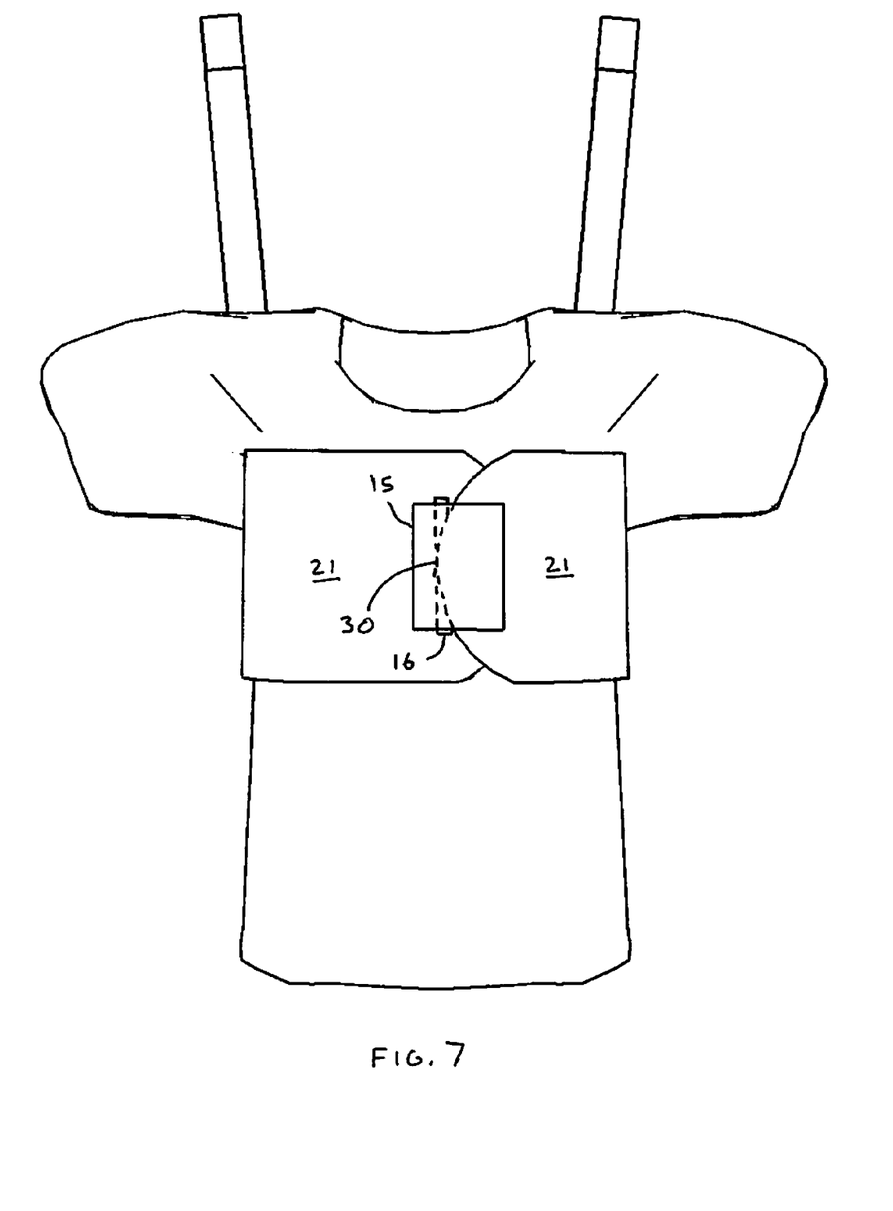
FIG. 7 is a front view of the preferred device shown at the step of FIG. 6.

The present invention is a method of strengthening the accessory muscles of the upper torso, also referred to herein as the chest, and a device used to perform the method. Referring to FIGS. 1 and 2, there is illustrated the preferred embodiment of the device, designated generally as 10, which is a wearable, compressive article comprising a wrap 11, at least one left shoulder strap 12, and at least one right shoulder strap 13. The wrap 11 is configured to wrap substantially entirely around a patient's chest and attach to itself to form a compressive loop. The wrap 11 is made of a substantially flexible and substantially elastic material, such as natural or synthetic rubber or another polymer, and is most preferably made of neoprene. Properties that relate to the flexibility and elasticity of the wrap 11, including the thickness and density of the material, may depend on the desired amount of resistance to be applied by the device. For example, the preferred thickness of the neoprene is about three millimeters, which is effective to address underdeveloped accessory muscles in children and adults as described below. In another example, the neoprene is about five millimeters thick, which provides more resistance for a rehabilitating patient that has injuries to major muscles but sufficient development in minor ones. The outer surface 21 of the wrap 11 may be partially or completely covered by a fastening fabric, such as the loop component of a VELCRO® fastener, in order to provide an attachment surface for one or more of the shoulder straps 12, 13, fastener 15, and markers 16, 17, described below. The inner surface 22 of the wrap 11 may be substantially smooth or may comprise ridges or other structures to improve ventilation across the inner surface 22.

The length L and width W of the wrap 11 are preferably fixed, but may be adjustable to fit patients of varying sizes. Alternatively, the wrap 11 may be accompanied by a sizing chart or have a sizing chart printed on it, in order to customize the dimensions of the wrap 11 properly for a particular patient. Preferably, the length L of the wrap 11 is long enough to encircle the patient's chest and leave an additional four to six inches of material for attachment and adjustment. The width W is sufficient to apply the compression described below to the targeted muscle fibers. In most patients, the wrap 11 must therefore cover the upper torso from the first rib to the bottom of the rib cage. If this width W results in the wrap 11 covering a portion of the upper torso above the axilla, which will typically be the case, the wrap 11 may comprise arm holes 14 that extend to slightly below the axilla, allowing the device 10 to fit comfortably. The arm holes 14 may be prefabricated integrally with the wrap 11, or the arm holes 14 may be cut by the therapist before use. In the latter embodiment, the wrap 11 may have a cutting template printed on the surface in order to help the therapist properly locate the arm holes 14. In another embodiment, one arm hole 14 may be prefabricated and the other arm hole 14 may be cut by the therapist, in order to customize the device 10 for a specific patient.

The wrap 11 has a releasable fastener 15 to removably attach the wrap 11 to itself around the patient's chest. The fastener 15 may be any mechanism configured to attach to and detach from at least one end of the wrap 11 so that the diameter of the compressive loop is adjustable. In the preferred embodiment, the fastener 15 is a discrete piece of fastening fabric made of the hook component of a VELCRO® or similar fastener. The preferred fastener 15 is therefore completely removable from the wrap 11. In another embodiment, the faster 15 comprises a plurality of strips of fastening fabric. In still other embodiments, the fastener 15 may be permanently attached to one end of the wrap 11, or may be permanently attached in multiple places if the fastener 15 has cooperating components. Example alternative embodiments of the fastener 15 include removably adhesive fabric, metal or plastic hook-and-eye closures, metal or plastic clips, movable magnets, buttons, and zippers, provided the fastener 15 is configured to allow adjustment of the diameter of the compressive loop.

The left shoulder strap 12 and right shoulder strap 13 fit over the patient's shoulders, such that the device 10 is worn like a vest. The shoulder straps 12, 13 are configured to hold the wrap 11 in place and keep it from sliding down the patient's chest. As such, the shoulder straps 12, 13 preferably fit closely over the patient's shoulders, and most preferably are adjustable so they can be repositioned as the wrap 11 is tightened during therapy. Alternatively, the shoulder straps 12, 13 may be permanently attached to the wrap 11. The shoulder straps 12, 13 may be made of any substantially flexible material, and most preferably are made of the same neoprene as the wrap 11. Preferably, the shoulder straps 12, 13 are covered in the same fastening fabric as used on the wrap 11. The shoulder straps 12, 13 may be removably attached to the wrap 11 at the anterior and posterior of the patient by strap fasteners 18. The strap fasteners 18 are preferably hook-and-loop fasteners like the fastener 15, but alternatively may be buckles, laces or another suitable fastener.

The device 10 may have one or more markers 16, 17 attached to the wrap 11 to indicate the proper fastener 15 position at any stage of therapy. At least a tension marker 16 may be used to indicate the placement of the fastener 15 as described below. In the preferred embodiment, the device 10 further comprises a new tension marker 17 used to mark the incremental translation of the fastener 15 while it is being determined, as described below. The markers 16, 17 are preferably color coded to facilitate adjustment of the device 10. In the preferred embodiment, the markers 16, 17 comprise a hook-fastening fabric on one side and a loop-fastening fabric on the opposite side, so that the markers 16, 17 may removably attach both to the outer surface 21 of the wrap 11 and to the preferred fastener 15. The markers 16, 17 may have a predetermined width, such as 0.25 or 0.5 inches, that correspond to the incremental adjustment distances used in the method described below. This allows the therapist to measure the adjustment without a ruler or other measurement aid. In still other embodiments, the device 10 may further comprise additional markers to aid in the adjustment of the device 10, such as an interval scale printed on the wrap 11 to indicate the distance the fastener 15 or markers 16, 17 have been moved.

The device 10 addresses muscular disuse, inhibition, weakness, underdevelopment, and other inoperativeness by training the accessory muscles to activate properly, and then strengthening those muscles. The muscles and muscle fibers that may be directly or indirectly trained and strengthened by using the device include: the sternocleidomastoid, which raises the sternum to assist in forced inspiration; the anterior and middle scalenes, which elevate the first rib with inspiration; the posterior scalene, which elevates the second rib with inspiration; the levatores costarum, which elevate the thoracic rib cage; the external, internal, and innermost intercostales, and the transversus thoracis, which elevate and depress the rib cage during breathing; the subcostales, which depress the ribs during expiration; the serratus posterior superior, which elevates the ribs during inspiration; and the serratus posterior inferior, which depresses the lower ribs to aid in expiration These muscles are trained to activate by applying substantially uniform compression around the chest, stimulating the body's innate reaction to expand the chest cavity. This reaction comprises activating accessory muscles, including some or all of those listed above, to elevate the rib cage and force inspiration. The accessory muscles remain active for as long as compression is sustained, so that inspiration and expiration are managed using the accessory muscles. Proper use may significantly improve many disorders, but marked improvement is particularly experienced regarding the following: diminished tidal volume; diminished inspiratory volume; diminished pulmonary ventilation during both exertion and rest; flared ribs; pectus excavatum, including following repair surgeries; diminished motor skills, particularly in the arms; diminished breath suspension; and low tone.

The device 10 should be used under the direct supervision of a therapist, such as a physical therapist, occupational therapist, or speech therapist, who has been trained to use the device 10. The therapist trains the patient, or the patient's caregiver, how to use the device 10. References to "patient" in the following explanation will be understood to refer to the person who is applying the device to the patient. Referring to FIGS. 3-7, to use the device 10, the therapist preferably first instructs the patient to put on a shirt or other cloth barrier that prevents skin contact with the device 10. This is done to reduce or eliminate irritation or allergic reaction of the skin, which may be caused by the materials used. Additionally, neoprene is an insulator, which may make the patient warm at times, and the barrier absorbs sweat and other moisture. The therapist lays the device 10 out flat, with the inner surface 22 facing up. The shoulder straps 12, 13 may be attached to the posterior of the wrap 11 at this point. The fastener 15 is preferably attached to the first end 30 of the wrap 11. The tension marker 16 is attached near the second end 31 of the wrap 11, at an initial distance D from the second end 31, such that the wrap 11 forms a loop with a circumference approximately equal to the circumference of the patient's chest when the first end 30 just touches the tension marker 16. The therapist instructs the patient to lie face-up on the wrap 11, with the top of the wrap 11 at about shoulder level. The therapist then pulls both ends 30, 31 of the wrap 11 forward to test whether the patient's arms are seated in the arm holes 14.

With the arms properly seated, the therapist places the second end 31 of the wrap 11 on the patient's chest and folds the first end 30 of the wrap 11 over the second end until the first end 30 just touches the tension marker 16. The therapist then pulls the second end 31 tighter against the patient's chest, moving the tension marker 16 about 0.25 to 0.5 inches with respect to the first end 30, and secures the fastener 15 to the outer surface 21 of the wrap 11. At this point, the first end 30 of the wrap 11 just covers the tension marker 16, see FIG. 7, and a slight amount of tension, or compression, is applied to the patient's chest by the wrap 11. The therapist closely observes the rise and fall of the patient's chest and belly. Chest movement indicates that the core muscles are activated at the least amount of tension necessary to activate them. If the chest is not rising and falling with each breath, there is not enough tension to activate the accessory muscles. The therapist then tightens the wrap 11 by loosing the fastener 15, pulling the first or second end to move the tension marker 16 another 0.25 inches, and refastens the fastener 15. The therapist checks for chest movement again and repeats the tightening process until chest movement is achieved. If chest movement is not achieved, it is likely that the therapist either passed the correct setting without noticing chest movement, or is using a wrap 11 that applies too much tension at the lowest setting. The therapist should release the fastener 15 and start the process over, possibly with a wrap 11 comprised of thinner material.

In the preferred embodiment, when chest movement is observed, the therapist marks the fastener's 15 new location with the new tension marker 17, looses the fastener 15, and may then move the tension marker 16 to where the new tension marker 17 is. The therapist also fastens the shoulder straps 12, 13 in their proper position to hold the wrap 11 in place without placing tension on the shoulders. The patient may now put on the device without therapist supervision by placing the fastener 15 at the tension marker's 16 position.

For the first two weeks, the patient wears the device 10 at the first set tension for between 1.5 and two hours per day at least six days per week. The requisite two hours may be continuous or non-continuous. After two weeks, the tension level is reassessed using the method above. Specifically, the therapist tightens the wrap 11 about 0.25 to 0.5 inches, as is tolerable by the patient. The new tension level is proper when the patient demonstrates mid- and upper-chest motion during inspiration and expiration on at least 50% of the patient's breaths. If there is movement on less than 50% of the patient's breaths, the new tension setting is not tolerable and tension must be re-set to the prior setting. The device is then worn for about three continuous or non-continuous hours per day, at least six days per week, and the tension level is reassessed as above every four weeks. As the patient wears the device 10, the accessory muscles strengthen, allowing greater expansion of the ribcage and a larger volumetric draw of air into the lungs. The compression of the wrap 11 therefore gradually increases throughout the month as the patient takes larger breaths, the accessory muscles working harder against the resistance of the wrap 11. The regimen proceeds for, typically, between 12 and 24 months, depending on the desired results. For example, in a regimen intended to account for a young child's lost tummy time as an infant, 24 months of proper use of the device 10 will result in between 1800 and 1900 hours of muscle development, which may be sufficient to correct breathing, head control, postural, speech, and motor skill deficiencies in the child. The effectiveness of the treatment may be measured using any known test in a therapy regimen.

The device 10 should not be used in a therapy regimen for any patient having an inability to tolerate the wearing of the device 10 for any reason. Examples of such a reason include: allergy to the device 10 material; certain compromises of the cardiac or cardiovascular systems; brittle bones or bones that are otherwise susceptible to fracture; irregular respiration or breathing patterns of a neurologic origin; and certain compromises of the respiratory system, such as a collapsed lung, lung tube, or pneumonia.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention will include all embodiments falling within the scope of the appended claims.

I claim:

1. A therapeutic method for developing a patient's accessory muscles, the method comprising:
   a) a therapist securing a device around the patient's chest so that the device applies a therapeutically effective amount of compression to the patient's chest to activate one or more of the accessory muscles, the device comprising an adjustable compressive wrap;
   b) having the patient wear the device at the effective amount of compression during a predetermined length of time each day of a specified wear schedule; and
   c) after the specified wear schedule, the therapist adjusting, at one or more time intervals, the device to increase the amount of continuous compression applied to the patient's chest.

2. The method of claim 1 wherein the device comprises a fastener attached to the wrap and configured to removably attach the wrap to itself to form a substantially elastic loop.

3. The method of claim 2 wherein securing the device comprises:
   a) laying the patient flat on the patient's back;
   b) the therapist wrapping the device around the chest such that the device substantially covers the chest from the patient's first rib to the bottom of the patient's rib cage; and
   c) wherein activating one or more of the accessory muscles comprises, until observing that the patient's chest rises with inspiration and falls with expiration on 50% or more of the patient's breaths:
      i. the therapist tightening the wrap a predetermined increment;
      ii. the therapist attaching the fastener to the wrap to form the elastic loop, the elastic loop applying compression to the patient's chest; and
      iii. the therapist observing the patient's chest movement.

4. The method of claim 3 wherein the predetermined increment is about 0.25 inches.

5. The method of claim 3 wherein securing the device further comprises the therapist placing a barrier between the device and the patient's skin such that the device substantially contacts the barrier and not the patient's skin.

6. The method of claim 3 wherein the therapist adjusting, at one or more time intervals, the device to increase the amount of continuous compression applied to the patient's chest if the patient can tolerate an increase.

7. The method of claim 6 wherein adjusting the device comprises:
   a) the therapist tightening the wrap by the predetermined increment;
   b) the therapist attaching the fastener to the wrap to re-form the elastic loop at a higher compression than was previously applied;
   c) the therapist observing the patient's chest movement; and
   d) if the patient's chest is not observed to move on 50% or more of the patient's breaths, the therapist loosening the wrap by the predetermined increment and re-attaching the fastener to the wrap.

8. The method of claim 7 wherein adjusting the device further comprises:
   a) the therapist tightening the wrap again by the predetermined increment if the patient's chest is observed to move on 50% or more of the patient's breaths;
   b) the therapist attaching the fastener to the wrap to re-form the elastic loop at a higher compression than was previously applied;
   c) the therapist observing the patient's chest movement; and
   d) if the patient's chest is not observed to move on 50% or more of the patient's breaths, the therapist loosening the wrap by the predetermined increment and re-attaching the fastener to the wrap.

9. The method of claim 8 wherein the predetermined increment is between 0.25 and 0.5 inches.

10. The method of claim 6 wherein the one or more time intervals comprise:
    a) a first interval of about 2 weeks; and
    b) one or more second intervals of about 4 weeks, the second interval being subsequent to the first interval.

11. The method of claim 10 wherein:
    a) the first interval comprises a first wear schedule of 1.5 to 2 continuous hours per day, for at least 6 days per week; and
    b) the second interval comprises a second wear schedule of 3 continuous hours per day, for at least 6 days per week; and wherein the patient wears the device for an amount of time according to the first and second wear schedules.

12. A therapeutic method for developing a patient's accessory muscles, the method comprising:
    a) having the patient wear a barrier around the chest;
    b) laying the patient flat on the patient's back;
    c) placing a therapy device under the patient's back, the therapy device comprising:
       i. an adjustable compressive wrap having a first end, a second end, an inner surface, and an outer surface;
       ii. a left arm hole and a right arm hole formed into the wrap;
       iii. a left shoulder strap and a right shoulder strap both attached to the wrap and configured to fit over the patient's shoulders;
       iv. a fastener attached to the first end of the wrap and configured to removably attach the wrap to itself to form a loop;
       v. a tension marker removably attached to the outer surface of the wrap proximate the second end; and
       vi. a new tension marker removably attached to the outer surface of the wrap;
       such that the inner surface of the wrap contacts the barrier around the chest;
    d) aligning the arm holes with the patient's arms, so that the alignment of the wrap will encircle the patient's chest from the first rib to the bottom of the rib cage;
    e) wrapping the wrap around the patient's chest so that the wrap contacts the barrier but does not apply compression to the chest;
    f) activating the accessory muscles of the patient by, until it is observed that the patient's chest rises with inspiration and falls with expiration on 50% or more of the patient's breaths:
       i. a therapist tightening the wrap such that the tension marker moves about 0.25 inches with respect to the fastener;
       ii. the therapist securing the wrap to apply a therapeutically effective amount of continuous compression to the patient's chest by attaching the fastener to the outer surface of the wrap proximate the second end;
       iii. the therapist observing the patient's chest movement;

g) marking the position of the fastener with the new tension marker;
h) replacing the new tension marker with the tension marker;
i) having the patient wear the device with the fastener attached at the tension marker to apply the effective amount of compression during a first predetermined length of time each day of a first treatment duration;
j) after the first treatment duration, reassessing the device, the reassessing comprising:
   i. the therapist tightening the wrap such that the tension marker moves about 0.25 inches with respect to the fastener;
   ii. the therapist securing the wrap by attaching the fastener to the outer surface of the wrap proximate the second end;
   iii. checking the patient's chest movement;
   iv. if it is observed that the patient's chest rises with inspiration and falls with expiration on 50% or more of the patient's breaths:
      (1) the therapist tightening the wrap such that the tension marker moves another 0.25 inches with respect to the fastener;
      (2) the therapist securing the wrap by attaching the fastener to the outer surface of the wrap proximate the second end; and
      (3) the therapist observing the patient's chest movement;
   v. if it is observed that the patient's chest does not move on 50% or more of the patient's breaths:
      (1) the therapist loosening the wrap such that the tension marker moves 0.25 inches with respect to the fastener; and
      (2) the therapist securing the wrap by attaching the fastener to the outer surface of the wrap proximate the second end;
   vi. marking the position of the fastener with the new tension marker; and
   vii. replacing the new tension marker with the tension marker;
k) after reassessing the device, having the patient wear the device with the fastener attached at the tension marker to apply the re-assessed therapeutically effective amount of continuous compression to the patient's chest during a second predetermined length of time each day of a second treatment duration; and
l) reassessing the device again at one or more time intervals.

13. The method of claim 12 wherein:
a) the first treatment duration is two weeks and comprises a first wear schedule of 1.5 to 2 continuous hours per day, at least 6 days per week; and
b) the second treatment duration is four weeks and comprises a second wear schedule of 3 continuous hours per day, at least 6 days per week;
such that the patient wears the device for an amount of time according to the first or second wear schedule.

* * * * *